United States Patent
Sobotowski et al.

(10) Patent No.: US 7,487,663 B2
(45) Date of Patent: Feb. 10, 2009

(54) METHOD FOR SELECTING FUEL TO BOTH OPTIMIZE THE OPERATING RANGE AND MINIMIZE THE EXHAUST EMISSIONS OF HCCI ENGINES

(75) Inventors: Rafal A. Sobotowski, Media, PA (US); Charles H. Schleyer, Lincoln University, PA (US); Kevin P. Duffy, Metamora, IL (US); Michael P. Liechty, Chillicothe, IL (US)

(73) Assignees: ExxonMobil Research & Engineering Co., Annandale, NJ (US); Caterpillar Inc., Peoria, IL (US)

(*) Notice: Subject to any disclaimer, the term of this patent is extended or adjusted under 35 U.S.C. 154(b) by 373 days.

(21) Appl. No.: 11/407,525

(22) Filed: Apr. 20, 2006

(65) Prior Publication Data
US 2007/0246005 A1    Oct. 25, 2007

(51) Int. Cl.
*G01N 33/22*    (2006.01)
(52) U.S. Cl. .................................................... 73/35.02
(58) Field of Classification Search ................ 73/35.02; 123/304
See application file for complete search history.

(56) References Cited

U.S. PATENT DOCUMENTS

| | | | | |
|---|---|---|---|---|
| 2003/0052041 A1 | 3/2003 | Erwin et al. | ................... | 208/15 |
| 2004/0231650 A1 | 11/2004 | Gray, Jr. | ................ | 123/568.12 |
| 2004/0261762 A1* | 12/2004 | Sloane et al. | ................ | 123/304 |
| 2006/0180121 A1* | 8/2006 | Wickman et al. | ............ | 123/299 |
| 2007/0256648 A1* | 11/2007 | Sun et al. | ..................... | 123/1 A |

FOREIGN PATENT DOCUMENTS

CH    WO 2005/059063 A1    6/2005

OTHER PUBLICATIONS

Koji Kitano, et al.; "Effects of Fuel Properties on Premixed Charge Compression Ignition Combustion in a Direct Injection Diesel Engine"; JSAE 20030117, SAE 2003-01-1815; 2003, pp. 1-7.

Mingfa Yao, et al.; "The Effect of PRF Fuel Octane Number on HCCI Operation"; Reprinted from Homogeneous Charge Compression Ignition (SP-1896); SAE International Powertrain & Fluid Systems, Conference & Exhibition, Tampa, Florida, Oct. 25-28, 2004; SAE Technical Paper Series 2004-01-2992; pp. 1-9.

Mingfa Yao, et al.; "Experimental Study on the Effects of EGR and Octane Number of PRF Fuel on Combustion and Emission Characteristics of HCCI Engines"; 2005 SAE World Congress, Detroit, Michigan, Apr. 11-14, 2005; SAE International, SAE Technical Paper Series 2005-01-0174; pp. 1-14.

Daisuke Kawano, et al.; "Ignition and Combustion Control of Diesel HCCI"; 2005 SAE International, 2005-01-2132; pp. 1-7.

(Continued)

*Primary Examiner*—Erick Solis
(74) *Attorney, Agent, or Firm*—Watov & Kipnes, P.C.; Kenneth Watov

(57) ABSTRACT

Operation of a DI HCCI engine is optimized for maximizing load capability and load ranges via matching fuel ignitability with the compression ratio of the engine.

36 Claims, 7 Drawing Sheets

OTHER PUBLICATIONS

M.J. Atkins and C.R. Koch; "The Effect of Fuel Octane and Dilutent on Homogeneous Charge Compression Ignition Combustion"; Proc. ImechE. vol. 219 Part D: J. Automobile Engineering; 2005; pp. 665-675.

Standard Test Method for Determination of Ignition Delay and Derived Cetane Number (DCN) of Diesel Fuels Oils by Combustion in a Constant Volume Chamber; ASTM International Designation D 6890-04; pp. 1-15.

"An Experimental Study on the Effects of Combustion and Fuel Factors on DI Diesel Engine Performance", SAE Technical Papers 2004-08-0375; JSAE Technical Paper 20045776 (published in Japan).

* cited by examiner

| PARAMETER | TEST METHOD | GASOLINE FUELS | | | |
|---|---|---|---|---|---|
| | | G11 | G12 | G13 | G23 |
| DENSITY @ 15.6°C, g/cm3 | D4052 | 0.7121 | 0.7111 | 0.7101 | 0.7388 |
| DERIVED CETANE NUMBER | D6890 | 27.2 | 29.6 | 32.0 | 32.4 |
| RON | D2699 | 81.4 | 73.8 | 66.0 | 65.0 |
| MON | D2700 | 79.9 | 72.3 | 64.0 | 60.0 |
| (R+M)/2 | - | 80.7 | 73.1 | 65.0 | 62.5 |
| DISTILLATION, °C      10% | D86 | 65 | 66 | 63 | 68 |
| 50% | | 97 | 96 | 94 | 99 |
| 90% | | 146 | 148 | 151 | 150 |
| SULFUR, ppm | D2622 | 48 | 67 | 85 | 40 |
| PIONA, %     PARAFFINS | D6839 | 79.3 | 77.8 | 76.2 | 60.3 |
| CYCLOPARAFFINS | | 3.7 | 6.0 | 8.6 | 2.7 |
| OLEFINS | | 3.3 | 2.8 | 2.4 | 1.4 |
| AROMATICS | | 13.7 | 13.4 | 12.7 | 35.6 |
| BENZENE | | 0.8 | 0.9 | 0.9 | 1.5 |

FIG. 2

| PARAMETER | TEST METHOD | DIESEL FUELS | | | | | |
|---|---|---|---|---|---|---|---|
| | | D12 | D12-C | D13 | D13-B | D14 | D15 |
| DENSITY @ 15.6°C, g/cm3 | D4052 | 0.9103 | 0.8799 | 0.8200 | 0.8251 | 0.8388 | 0.8682 |
| CETANE NUMBER | D613 | 26.4 | 36.5 | 27.8 | 34.2 | 45.9 | <19.4 |
| DERIVED CETANE NUMBER | D6890 | 29.6 | 37.1 | 33.1 | 37.2 | 45.0 | 23.4 |
| DISTILLATION, °C     10% | D86 | 225 | 218 | 225 | 220 | 213 | 223 |
| 50% | | 256 | 248 | 265 | 258 | 244 | 268 |
| 90% | | 315 | 312 | 301 | 303 | 308 | 309 |
| SULFUR, ppm | D2622 | 242 | 153 | 124 | 94 | 11 | 23 |
| SFC AROMATICS, %     1-RING | D5186 | 25.2 | 24.6 | 8.6 | 12.9 | 23.1 | 27.0 |
| 2+-RING | | 40.2 | 28.3 | 5.3 | 6.6 | 11.7 | 27.2 |
| TOTAL | | 65.4 | 52.9 | 13.9 | 19.5 | 34.8 | 54.2 |

FIG. 3

| NUMBER OF CYLINDERS | 1 |
|---|---|
| DISPLACEMENT | 2.44 dm$^3$ |
| BORE/STROKE | 137/165 mm |
| VALVES/CYLINDER | 4 |
| SWIRL RATIO | ~0.4 |

| FUEL SERIES NAME | FUELS INCLUDED IN SERIES | AVERAGE AROMATIC CONTENT |
|---|---|---|
| HIGH AROMATICS DIESEL | D12, D12-C | 59.2% |
| LOW AROMATICS DIESEL | D13, D13-B | 16.7% |
| HIGH AROMATICS GASOLINE | G23 | 35.6% |
| LOW AROMATICS GASOLINE | G11, G12, G13 | 13.3% |

FIG. 11

| FUEL SERIES NAME | AVERAGE AROMATIC CONTENT | AVERAGE SMOKE DATA | | | | | |
|---|---|---|---|---|---|---|---|
| | | LIGHT LOAD | | MEDIUM LOAD | | HEAVY LOAD | |
| | | 1200 rpm | 1800 rpm | 1200 rpm | 1800 rpm | 1200 rpm | 1800 rpm |
| HIGH AROMATICS DIESEL | 59.2% | 0.02 | 0.01 | 0.18 | 0.10 | 0.65 | 0.55 |
| LOW AROMATICS DIESEL | 16.7% | 0.03 | 0.00 | 0.07 | 0.02 | 0.41 | 0.23 |
| HIGH AROMATICS GASOLINE | 35.6% | 0.01 | 0.00 | 0.05 | 0.09 | 0.06 | 0.08 |
| LOW AROMATICS GASOLINE | 13.3% | 0.00 | 0.00 | 0.01 | 0.00 | 0.01 | 0.01 |

FIG. 12

METHOD FOR SELECTING FUEL TO BOTH OPTIMIZE THE OPERATING RANGE AND MINIMIZE THE EXHAUST EMISSIONS OF HCCI ENGINES

TECHNICAL FIELD

The present disclosure is broadly related to methods for controlling the operation of internal combustion engines, and is more particularly directed toward methods for selecting a fuel for optimizing the control of the operation of homogeneous charge compression ignition (HCCI) engines.

BACKGROUND

Internal-combustion engines fall into four categories, defined by the amount of mixing in the air/fuel charge and how the charge is ignited. In a standard gasoline engine air and fuel are premixed into a well-mixed charge that is ignited with a spark. In a standard diesel engine fuel is sprayed into the cylinder during the piston's compression stroke. Air and fuel are not well mixed when the rising temperature from compression induces burning. In the homogenous charge compression ignition (HCCI) engine air and fuel are well mixed before self-ignition due to compression. In an HCCI engine the air and fuel can be premixed as in a gasoline engine or fuel can be directly injected like a diesel but earlier to allow better air/fuel mixing before ignition. Better air/fuel mixing produces much lower NOx and PM emissions compared to standard diesel combustion where rich fuel/air pockets lead to soot formation, and flame surrounding the injected fuel leads to high NOx. HCCI has better fuel economy than a gasoline engine because there is no throttling, and because higher compression ratios can be used.

The main challenges for HCCI are both too rapid combustion, and lack of a triggering ignition event. Once the temperature in the HCCI engine cylinder is sufficiently high, the premixed air/fuel mixture combusts rapidly. If combustion is too rapid then high pressure rise rates can occur causing excessive noise and potential engine damage. The lack of an ignition triggering event makes it more difficult to control an HCCI engine. In a gasoline engine a spark triggers ignition, while in a diesel engine fuel injected into hot compressed air triggers ignition. These measures cannot be used to control ignition timing and duration in an HCCI engine.

Another challenge for HCCI engines is their limited load range caused by the use of high excess air/fuel ratios and/or high EGR rates to control combustion phasing, cylinder pressure, rate of cylinder pressure rise and/or NOx emissions.

Currently, some of the challenges facing HCCI engines include:

Limited load range;

Lack of universal, yet practical, measures of ignition quality of HCCI fuels; and Excessive particulate/smoke emissions during operation on diesel boiling range fuels, especially at high engine loads.

HCCI technology is still at a relatively early stage of development, yet holds great promise due to its excellent exhaust emission and fuel efficiency characteristics. Different versions/configurations of HCCI engines are being developed worldwide. Their commercialization has been held back mainly by the challenges of this technology, including limited load range, difficulties in controlling combustion phasing and excessive heat release rates. In order to address some of these challenges and opportunities related to HCCI, Caterpillar has entered into a cooperative research and development agreement with ExxonMobil Corporation, since the Fall of 2002. This disclosure is a result of their joint work.

In the following disclosure, diesel fuel is defined as a mixture of hydrocarbons which boil at atmospheric pressure over a temperature range within about 150° C. to 0.380° C., whereas gasoline is defined as a mixture of hydrocarbons which boil at atmospheric pressure over a temperature range within about 25° C. to 220° C.

HCCI engines are operated at high air/fuel ratios and/or high EGR rates for the purpose of controlling combustion phasing, peak cylinder pressure, rate of cylinder pressure rise and/or NOx emissions. This restricts the amount of fuel that can be burned in the course of an engine cycle and thus limits the maximum achievable engine loads. For example, HCCI engines operated on a typical 45 cetane number US diesel fuel can produce, at most, only ⅓ of the load attainable by comparable diesel engines, if the comparison is made at the same diesel-like compression ratio.

SUMMARY OF THE DISCLOSURE

An aspect of the disclosure is a method for selecting a fuel from amongst a plurality of fuels, for optimizing the operation of an HCCI engine. The method includes the steps of determining a derived cetane number (DCN) in accordance with ASTM method D6890 for a plurality of liquid hydrocarbon-based fuel formulas to be tested, to permit said fuels to be evaluated on the same scale; testing said plurality of fuel formulas to determine the autoignition properties of each relative to their respective DCN; and matching the fuel ignitability of the tested ones of said plurality of fuel formulas with the compression ratio (CR) of said HCCI engine, to determine the fuel formula enabling said engine to operate at the highest load and over the broadest load range, at a given CR.

Another aspect of the disclosure is a method for selecting a fuel formula for a plurality of HCCI engines. The method includes the steps of testing a plurality of fuels to determine the ignitability of each; and running each of said plurality of HCCI engines on each one of the tested said plurality of fuel formulas to determine for each engine of a given CR the fuel formula that maximizes the load capability and load range thereof.

BRIEF DESCRIPTION OF THE DRAWINGS

Various embodiments of the present disclosure are described with reference to the drawings, in which like items are identified by the same reference designation, wherein:

FIG. 2 is a table showing the properties of gasoline fuels tested;

FIG. 3 is a table showing the properties of diesel fuels tested;

FIG. 11 shows a table of the fuel series encountered in the curves of FIGS. 9 and 10; and FIG. 12 is a table showing average smoke data relative to the fuel series tested.

DETAILED DESCRIPTION

Figure 1:
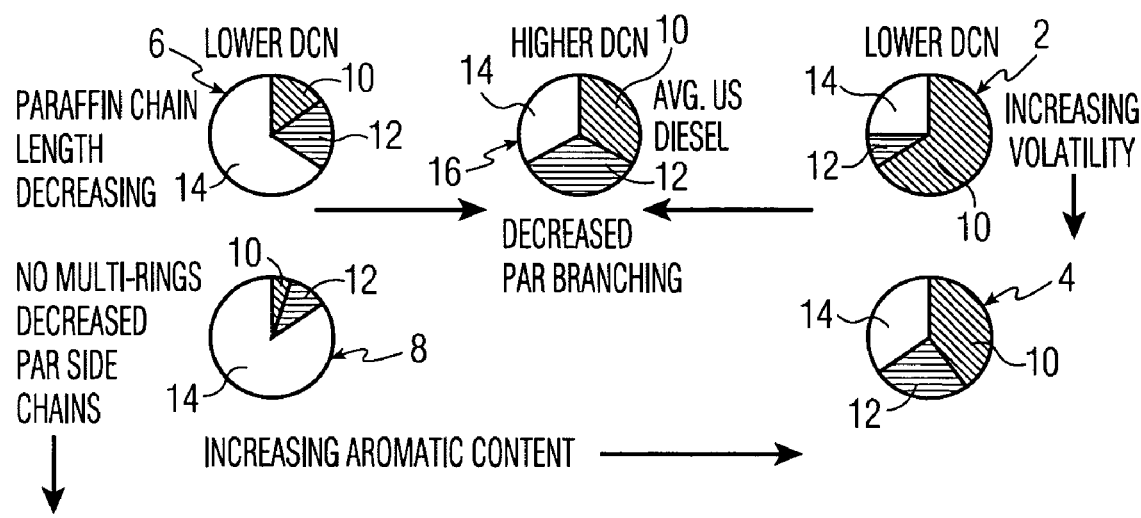
FIG. 1 shows a block schematic diagram of the selection of test fuels to evaluate the impact of fuel ignitability, chemistry, and volatility upon the operation of HCCI engines.

The use of a single parameter to characterize ignition quality of a wide range of fuels including both gasoline and diesel will benefit fuel suppliers, engine manufacturers, and the end users. Tests conducted by the inventors have demonstrated that liquid, hydrocarbon-based fuels which have the same derived cetane number determined according to ASTM method D6890 exhibit the same autoignition properties in the DI HCCI engine and enable HCCI operation up to the same maximum loads and over the same load ranges irrespective of their boiling range and hydrocarbon makeup. Derived cetane number by ASTM method D6890 is therefore proposed as a universal measure of autoignitability for both gasoline and diesel fuel used in DI HCCI engines. Although DI HCCI is described herein in more detail in relation to the disclosure, it should be understood that other types of HCCI engines (non-direct injection) may be utilized with the present disclosure to achieve similar results. Further, it should be understood that the terms DI HCCI or HCCI may be used interchangeably to describe any such HCCI engine.

Low-aromatic gasoline boiling range fuels emit essentially no smoke over the whole engine operating range, while high-aromatic gasoline emits small amounts of smoke at medium and heavy loads. Diesel boiling range fuels were found to emit significant amounts of smoke at high loads, and near stoichiometric operating conditions. In addition, an increase in the aromatic content of the fuel was shown to increase smoke emissions when the engine was operated on either diesel fuel or gasoline. Since a significant reduction of smoke emissions may eliminate the need for a particulate filter, or at least enable the use of a lower efficiency filter, a method of controlling smoke emissions from DI HCCI engines is proposed which requires that such engines be fueled with diesel fuel or gasoline where the aromatics content of the fuel is controlled below designated limits.

Fuel effects on DI HCCI engine performance has demonstrated that the highest maximum loads and the broadest load range can be realized through matching of ignition quality of the fuel with the compression ratio of the engine, and that a wide range of fuel chemistries can be used to achieve a broad range of engine operating loads. The test fuels were carefully designed to evaluate the impact of fuel ignitability, chemistry, and volatility on HCCI engine operation as shown in the pie charts of FIG. 1. Derived cetane number (DCN) was used as an ignability parameter. Fuels with high DCN ignite easily while fuels with low DCN are more resistant to ignition. The test fuels spanned a wide range of fuel ignitability, chemistry and volatility. Two volatility ranges were evaluated: high volatility fuels 4 and 8, in the gasoline boiling-range, and lower volatility fuels 2, 6, and 16, respectively, in the diesel boiling range. Within each volatility range, two fuel composition series were constructed with high aromatics and low aromatics content. Finally there were two levels of ignitability, fuel 16 with high DCN and fuels 2, 4, 8 and 6 with low DCN. More specifically, in the "Lower DCN" range, diesel fuel 2 has a higher aromatic content 10, and lower paraffin content 14, compared to gasoline fuel 4. Fuel 16 represents an average US diesel fuel, having nearly equal naphthene 12, aromatic 10, and paraffin content 14. Test fuel composition varies significantly with derived cetane number, volatility and aromatic content. The aromatic species in the more volatile fuels have one ring and short paraffinic side-chains, while the aromatics in the less volatile fuels have 1-3 rings and longer side-chains. Similarly the paraffinic species vary in molecular size and branching. The fractions labeled 12 are primarily naphthenes in diesel and are olefins and naphthenes in gasoline. All of these factors can influence fuel chemistry and ignition.

The test fuel properties are provided in tables shown in FIGS. 2 and 3, for gasoline fuels and diesel fuels, respectively. The fuels in FIGS. 2 and 3 correspond to the fuel experimental design depicted in FIG. 1. For example, with reference to FIG. 2, a series of gasoline fuel compositions G11, G12, and G13 were developed that each correspond to a fuel composition generally designated by reference numeral 8 in FIG. 1. In some cases series of fuels were developed to test smaller variations in composition and ignitability, generally designated as fuel compositions, 2, 6, and 8 in FIG. 1. Gasoline fuel composition G23 is related to the generally designated fuel composition 4 of FIG. 1. Similarly, with reference to FIG. 3, a series of diesel fuel compositions D12, D12-C, and D15 were developed that correspond to generally designated fuel compositions 2 of FIG. 1. Diesel fuel compositions D13 and D13-B were developed that correspond to generally designated fuel composition 6 of FIG. 1. Also, diesel fuel composition D14 corresponds to generally designated fuel composition 16 of FIG. 1. The derived cetane number (DCN) of diesel fuels ranged from 23.4 to 45.0 and aromatic content from 13.9 to 65.4%, as shown in FIG. 3. As shown in FIG. 2, the derived cetane number of gasolines ranged from 27.2 to 32.4, and (R+M)/2 octane number from 62.5 to 80.7, where the aromatic content was essentially identical (about 13%) for fuels G11, G12, and G13, but considerably higher (35.6%) for gasoline fuel composition G23. The respective distillation properties of test gasolines and diesel fuels were closely matched. Accordingly, the present inventors discovered that derived cetane number is a useful parameter to rate fuel ignitability because both gasoline and diesel fuels can be evaluated on the same scale.

The fuels described in FIGS. 1 through 3 provide a broad range of fuel chemistry with ignitability as determined by DCN that is intermediate between commercial gasoline and diesel. As illustrated in FIG. 1, the variation in volatility, ignitability and aromatic content have a significant impact on the nature of fuel compounds within broad compositional classes. For instance as shown in FIG. 1 increasing volatility decreases the size of paraffin molecules and reduces the length of paraffin side chains on aromatic molecules. Therefore the range of fuel composition is even broader than that described by the compositional variables FIGS. 2 and 3.

Providing equivalent ignitability across this broad compositional range using wide-boiling fuels was an important component of the testing.

A single-cylinder DI HCCI engine was used in these tests. Its specification is provided in the table shown in FIG. 4. For the compression ratio used in this investigation, the brake mean effective pressure (BMEP) targets established for this engine equaled 1600 kPa at 1200 rpm and 1400 kPa at 1800 rpm. The peak cylinder pressure and the rate of cylinder pressure rise were limited at 18 mega Pascals (MPa) and 3 MPa/degree crank angle, respectively. The coefficient of variation of indicated mean effective pressure (IMEP) was limited at 5%.

Figures 4, 5:
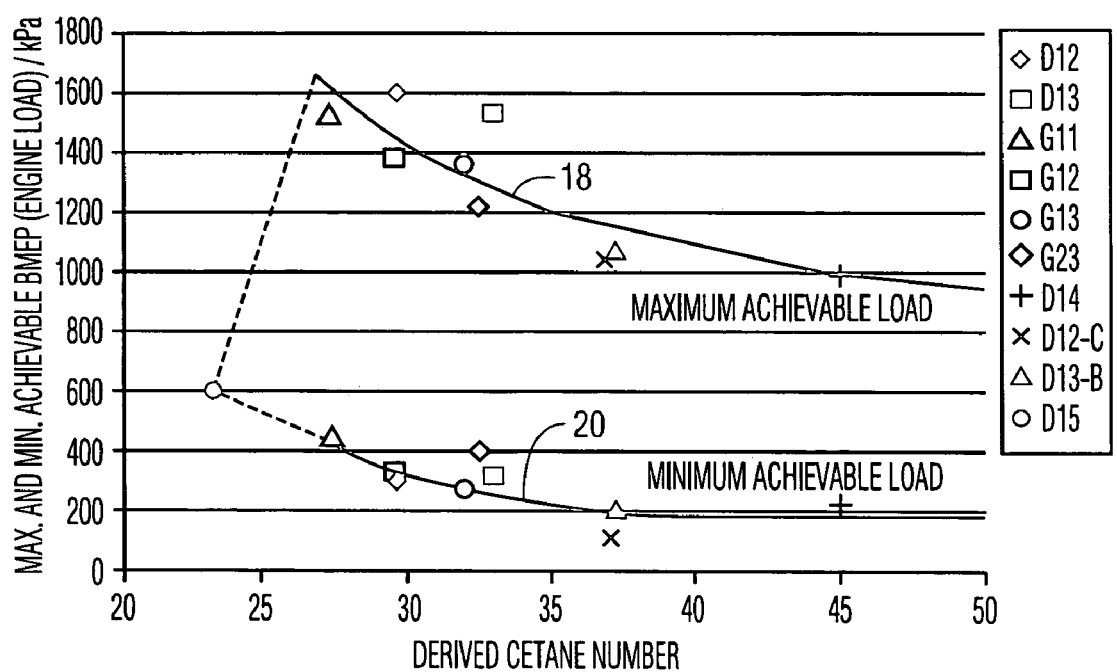
FIG. 4 is a table showing the specifications of a single-cylinder direct injection (DI) HCCI engine used in testing various fuels.
FIG. 5 shows maximum and minimum achievable brake mean effective pressure in kilo Pascals (BMEP kPa) or engine load versus Derived Cetane Number at 1200 rpm, and best fit curves for maximum and minimum achievable load are also shown.
Figure 6:
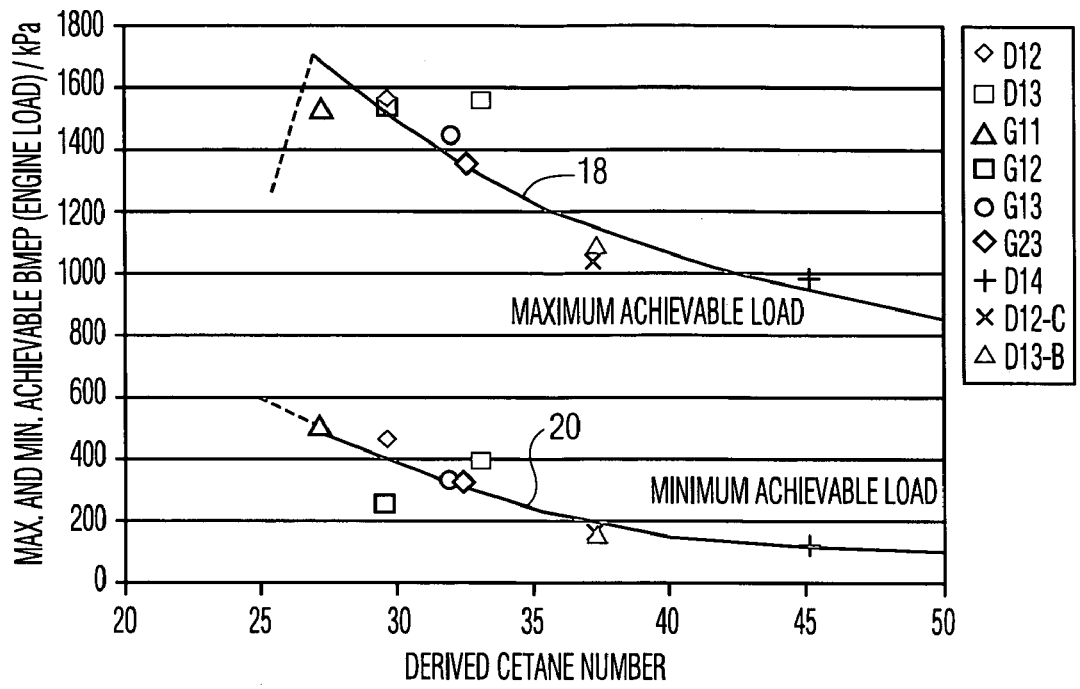
FIG. 6 shows maximum and minimum achievable Brake Mean Engine Pressure in kilo Pascals (BMEP kPa) or engine load versus Derived Cetane Number at 1800 rpm, and best fit curves for maximum and minimum achievable load are also shown.

As shown in FIGS. 5 and 6, both the maximum and the minimum achievable engine load curves 18, 20, respectively, increased as the derived cetane number of the fuel was reduced, for the fuels tested with DCN>27. Notably, the maximum achievable engine load increased at a faster rate resulting in widening of the engine's load range. At 1200 rpm, as shown in FIG. 5, achieving the target BMEP level of 1600 kPa required the use of a fuel whose derived cetane number was equal to or lower than about 28. At 1800 rpm, as shown in FIG. 6, attaining the target BMEP level of 1400 kPa required the use of a fuel whose derived cetane number was equal to or lower than about 32. The increase in maximum achievable load relative to operation on a typical US diesel fuel (fuel D14, DCN =45) was 60% (from about 1000 kPa to 1600 kPa) at 1200 rpm, and 40% (from about 1000 kPa to 1400 kPa) at 1800 rpm. At the same time, the load range increased by 55% (from 760 kPa to 1180 kPa) at 1200 rpm, and by 25% (from 840 kPa to 1050 kPa) at 1800 rpm.

Stable combustion could only be achieved using diesel fuel D15 (DCN=23.4) under one set of speed/load conditions, i.e., 1200 rpm and 600 kPa BMEP, indicating that a minimum DCN limit exists for successful HCCI operation (at least for diesel fuels) under the experimental conditions tested. It would be expected that a similar minimum DCN limit would also apply for a speed of 1800 rpm, as outlined in FIG. 6, since 1800 rpm would represent more severe operating conditions.

Reduction of fuel ignitability enabled higher load levels in the DI HCCI engine (for DCN>27) due to decreased need for EGR (exhaust gas recirculation) to control combustion phasing, thus making it possible to increase the amount of air in the cylinder charge. As a consequence, more fuel can be injected into the cylinder resulting in an increase of engine output. The minimum achievable engine loads increased with the reduction in fuel ignitability due to the increase in engine fueling which, together with retarded injection timing, was needed to ensure that the start of combustion occurred approximately at the TDC (top dead center) position of the piston and that NOx emissions were kept within acceptable limits.

Figure 7:
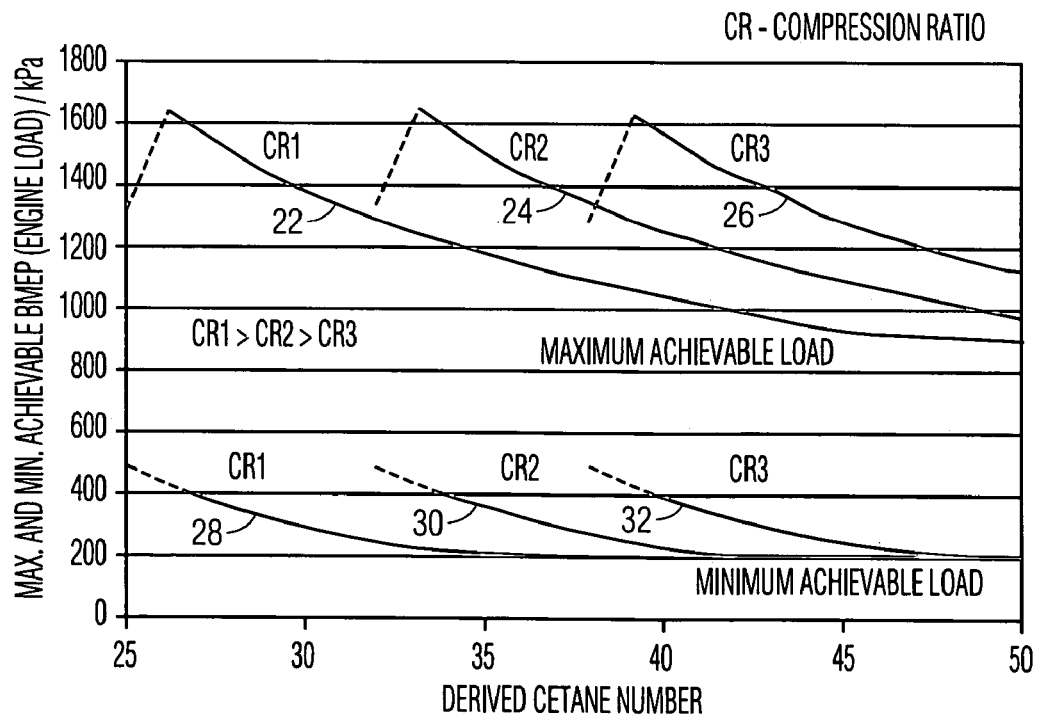
FIG. 7 shows curves for maximum and minimum achievable engine loads versus Derived Cetane Number at different engine compression ratios.

As FIGS. 5 and 6 demonstrate, fuel ignitability can be matched to the compression ratio of the DI HCCI engine to achieve the highest loads and the broadest HCCI load range. It is anticipated that with the change of compression ratio, the optimum fuel ignitability requirements will also shift, as shown schematically in FIG. 7, but that the principle of establishing those requirements will remain the same. In FIG. 7, maximum achievable load curves 22, 24, and 26 are shown for engine compression ratios CR1, CR2, and CR3, respectively. Also, in FIG. 7, minimum achievable load curves 28, 30, and 32 are shown for compression ratios CR1, CR2, and CR3, respectively. It is worth noting that while DCN was used in FIGS. 5, 6, and 7 to characterize ignition quality of the fuels, other measures of fuel ignitability, such as octane number or cetane number, can also be used. However, in a preferred embodiment, a wide variety of liquid hydrocarbon based fuels including diesel and/or gasoline fuel formulations, each having their fuel ignitability measured via a DCN, are arranged in a table identifying each fuel formulation, its DCN, and the compression ratio of a DI HCCI engine for which each fuel formulation provides optimum high engine load and load range.

In summary, one embodiment of this disclosure defines a method for matching the compression ratio and fuel ignitability requirements of DI HCCI engines for the purpose of increasing the maximum loads they can produce and maximizing the load range over which HCCI operation is possible. Fuels with reduced ignitability compared to typical US diesel allow higher engine compression ratios and more efficient operation. As a consequence, the unique fuel efficiency and exhaust emissions benefits of DI HCCI technology can be utilized to the greatest extent and with maximum efficiency.

The results depicted in FIGS. 5 and 6 were obtained with fuels encompassing a broad range of fuel chemistry and volatility. High engine loads were achieved with fuels using either low or high boiling range and with fuel aromatic content that varied from 12.7 to 65.4%. This demonstrates that a wide range of fuel composition and volatility can be utilized to achieve high engine loads.

It should be noted that ASTM Method D6890 entitled "Standard Test Method for Determination of Ignition Delay and Derived Cetane Number (DCN) of Diesel Fuel Oils by Combustion in a Constant Volume Chamber" covers DCN range of 33 to 60, for which its precision is defined. However, the equation which is used in this method to calculate DCN from ignition delay data was originally developed using fuels ranging in DCN from 0 to 100. In addition, this method does not apply to gasoline boiling range fuels, even though its calibration fuels fall within that range. Irrespective of these limitations and for the purpose of this disclosure, test methodology defined in ASTM method D6890 is applied both to gasoline and diesel boiling range fuels, over DCN range of 0 to 100.

Figure 8:
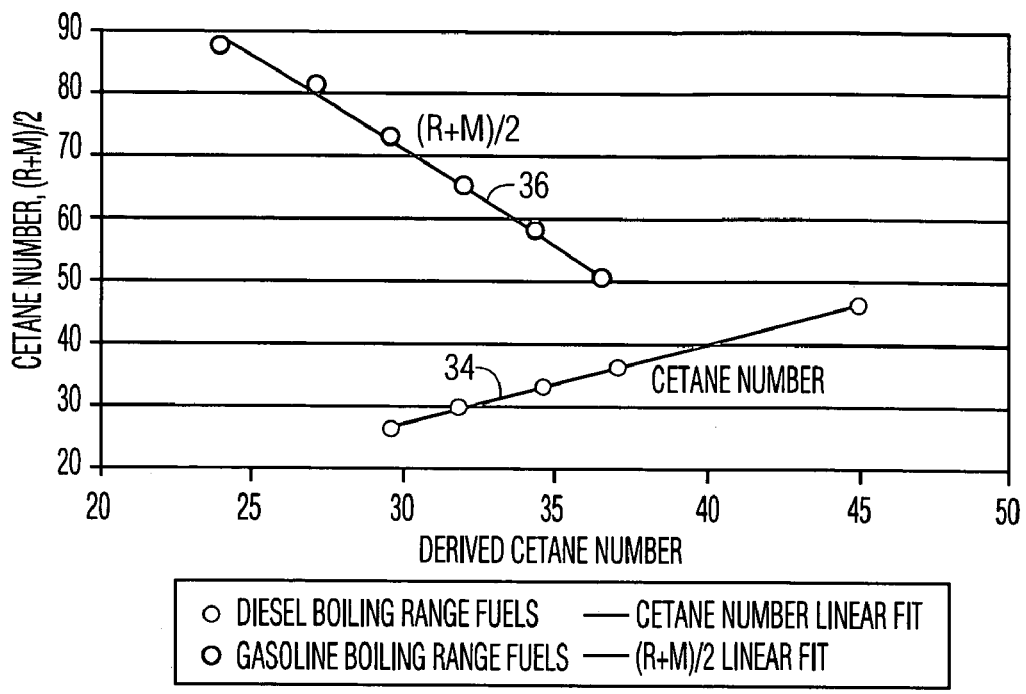
FIG. 8 shows curves of (R+M)/2 and Cetane Number versus Derived Cetane Number.

DI HCCI engines can be operated on a wide range of hydrocarbon-based liquid fuels ranging from gasoline to diesel fuel. In current practice, several parameters are used to characterize ignition quality of these fuels, e.g. motor octane number, research octane number and cetane number. Furthermore, octane number and cetane number rating methods are not applicable to fuels spanning wide ignition quality and distillation ranges. For example, gasolines are generally too resistant to autoignition to have their cetane number measured according to ASTM method D613. Diesel fuels are not volatile enough to have their octane numbers measured according to ASTM methods D2699 and D2700. Note that the relatively new ASTM method D6890 can be applied to fuels covering wide ignition quality and distillation ranges, providing a method of evaluating the ignition quality of gasoline and diesel fuels. FIG. 8 which shows the relationships between (R+M)/2 octane number (where R and M are ASTM D2699 research and ASTM D2700 motor octane numbers, respectively) and ASTM D6890 derived cetane number, and between ASTM D613 cetane number and ASTM D6890 derived cetane number for a variety of gasoline and diesel boiling range fuels.

FIG. 8 shows that a relationship can be established between DCN and (R+M)/2 octane, and between cetane number and DCN. Additional relationships can also be established between RON, MON and DCN using other functional forms. These ignition parameters, cetane number, RON, MON and (R+M)/2 or functional combinations of these parameters can also be used to match fuel ignitability with engine compression ratio.

Notably, tests have demonstrated that liquid, hydrocarbon-based fuels which have the same derived cetane number determined according to ASTM method D6890 exhibit the same autoignition properties in the DI HCCI engine and enable HCCI operation up to the same maximum loads and over the same load ranges irrespective of their boiling range and hydrocarbon makeup. This assertion is illustrated in FIGS. 5 and 6 for four gasolines and six diesel fuels whose properties are provided in the tables of FIGS. 2, and 3, respectively.

As previously mentioned, the use of a single parameter to characterize ignition quality of a wide range of fuels will benefit fuel suppliers, manufacturers of DI HCCI engines as well as the end users. Through use of this parameter, fuels for DI HCCI engines can now be rated in the same instrument, according to the same test method and used interchangeably based on their DCN, as long as the associated engines are designed to accommodate other properties of these fuels. The use of a single test methodology will simplify and reduce the cost of fuel development, DI HCCI engine development as well as fuel and engine quality control. Accordingly, derived cetane number by ASTM method D6890 is therefore proposed as a universal measure of autoignitability for both gasoline and middle distillate boiling range fuels used in DI HCCI engines. FIG. 8 shows curve 34 for cetane number, and curve 36 for (R+M)/2, versus derived cetane number, respectively.

Exhaust particulate (smoke) is considered a pollutant, and its emissions are regulated in many countries. Particulate emission standards are becoming increasingly stringent, necessitating the use of expensive particulate filters which also cause fuel efficiency losses. It is therefore advantageous to reduce engine-out emissions of exhaust particulate to eliminate the need for these devices or enable the use of less costly, lower efficiency filters.

Figure 9:
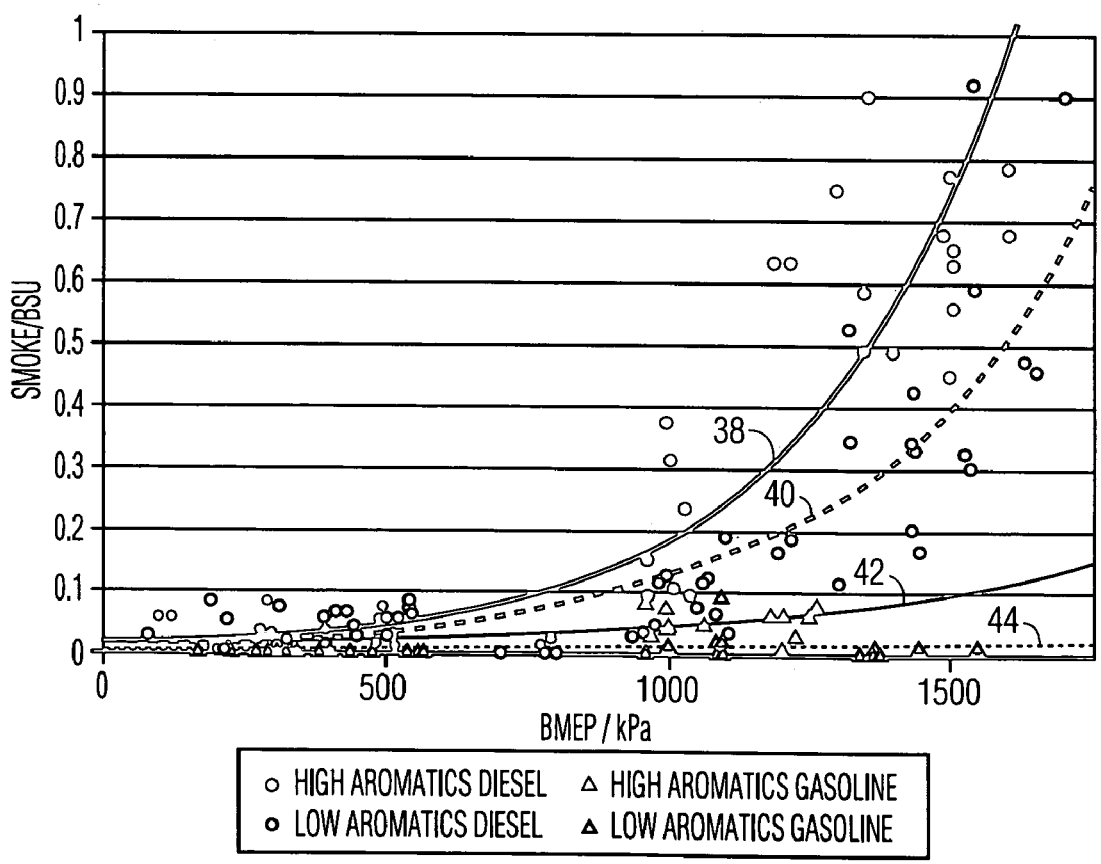
FIG. 9 shows curves for Smoke in Bosch Smoke Units (BSU) versus engine load (BMEP/kPa) for high aromatics diesel fuel, low aromatics diesel fuel, high aromatics gasoline fuel, and low aromatics gasoline fuel, at 1200 rpm.
Figure 10:
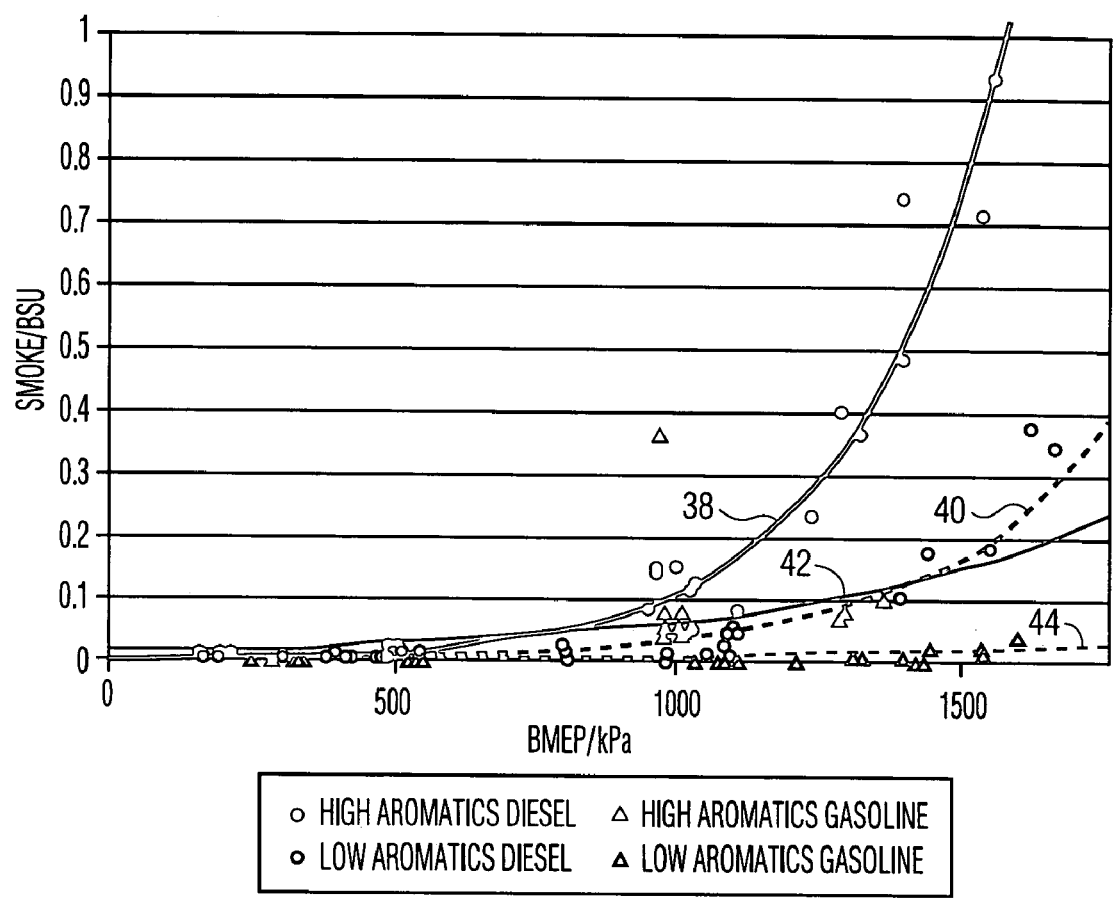
FIG. 10 shows smoke versus engine load for high aromatics diesel fuel, low aromatics diesel fuel, high aromatics gasoline fuel, and low aromatics gasoline fuel, respectively, at 1800 rpm.

As previously indicated, testing performed in a DI HCCI engine has demonstrated that low-aromatic gasoline emits essentially no smoke over the whole engine operating range, while high-aromatic gasoline emits small amounts of smoke at medium and heavy loads. Diesel fuel was found to emit significant amounts of smoke at high loads and at near stoichiometric operating conditions. In addition, an increase in the aromatic content of diesel fuel was shown to increase smoke emissions at medium and heavy loads. These observations are illustrated in FIG. 9 (1200 rpm) and FIG. 10 (1800 rpm) for several of the gasolines and diesel fuels listed in the tables of FIGS. 2 and 3, respectively. The smoke data in FIGS. 9 and 10 are plotted according to fuel type (diesel or gasoline) and relative aromatics content (high or low). In each of FIGS. 9 and 10, fitted curves 38, 40, 42, and 44 represent high aromatics diesel, low aromatics diesel, high aromatics gasoline, and low aromatics gasoline, respectively The fuels included in each series of data are listed in the table shown in FIG. 11, along with the series average aromatic content. Average smoke data was calculated for each series of fuels as shown in the table of FIG. 12, in which the average smoke number is tabulated for light loads (taken to be ≦600 kPa BMEP), medium loads (600 kPa<BMEP≦1200 kPa), and heavy loads (BMEP>1200 kPa), for speeds of 1200 rpm and 1800 rpm.

In view of these results, a method of controlling particulate emissions from DI HCCI engines is proposed which requires that such engines be fueled with diesel fuel or gasoline of controlled aromatics content. In the case of diesel boiling range fuel, it has been determined that the aromatic content should be lower than 60 wt. %, preferably lower than 40 wt. %, and more preferably lower than 20 wt. %. In the case of gasoline boiling range fuel, the aromatic content should be less than 40 wt. %, and preferably less than 20 wt. %.

Although various embodiments of the disclosure have been shown and described, they are not meant to be limiting. Those of skill in the art may recognize certain modifications to these embodiments, which modifications are meant to be covered by the spirit of the appended claims.

What is claimed is:

1. A method for selecting a fuel formulation from amongst a plurality of fuel formulations, for optimizing the operation of an HCCI engine, comprising the steps of:
    providing said plurality of fuel formulations including both gasoline fuel formulations and diesel fuel formulations for testing;
    determining a derived cetane number (DCN) in accordance with ASTM method D6890 as a universal measure of autoignitability for each of said plurality of fuel formulations for use in said HCCI engine, to permit said fuel formulations, to be evaluated on the same scale;
    testing said plurality of fuel formulations to determine the autoignition properties of each relative to their respective DCN; and
    matching the fuel ignitability of the tested ones of said plurality of fuel formulations with the compression ratio (CR) of said HCCI engine, to determine the fuel formulation enabling said engine to operate at the highest load and over the broadest load range, at a given CR.

2. The method of claim 1, further including controlling particulate emissions from said HCCI engine by making the aromatic content of diesel boiling range fuels less than 60 wt. %.

3. The method of claim 1, further including controlling particulate emissions from said HCCI engine by making the aromatic content of diesel boiling range fuels less than 40 wt. %.

4. The method of claim 1, further including controlling particulate emissions from said HCCI engine by making the aromatic content of diesel boiling range fuels less than 20 wt. %.

5. The method of claim 1 further including controlling particulate emissions from said HCCI engine by making the aromatic content of gasoline boiling range fuels less than 40 wt. %.

6. The method of claim 1, further including controlling particulate emissions from said HCCI engine by making the aromatic content of gasoline boiling range fuels less than 20 wt. %.

7. The method of claim 1, wherein in said determining step the plurality of fuel formulations have DCN numbers ranging from 0 to 100.

8. The method of claim 1, wherein said diesel fuel formulations have a DCN range from 23.4 to 45.0, respectively.

9. The method of claim 8, wherein said diesel fuel formulations have an aromatic content ranging from 13.9% to 65.4%.

10. The method of claim 1, wherein said gasoline fuel formulations have a DCN range from 27.2 to 32.4.

11. The method of claim 10, wherein said gasoline fuel formulations have an aromatic content ranging from 12.7% to 35.6%.

12. The method of claim 1, further including the steps of:
    running a plurality HOCI engines of different CR, each with said plurality of fuel formulations;

determining for each said engine the fuel formulation DCN that provides the highest load over the broadest load range; and tabulating the results of said determining step to match the CR of each of said plurality of HCCI engines with the optional fuel formulation DCN, thereby facilitating later selection by DCN of a fuel formulation for optimizing operation of a DI HOCI engine having a particular CR.

13. The method of claim 1, further including the step of:
establishing a relationship between the derived cetane numbers and (R+M)/2 octane.

14. The method of claim 1, further including the step of:
establishing a relationship between derived cetane numbers and cetane.

15. The method of claim 1, wherein said diesel fuel formulations are selected from a group consisting of formulations having a DCN range from 23.4 to 45, equivalent to a cetane number range from 19.4 to 45.9, an aromatic content ranging from 13.9% to 65.4%, and combinations thereof.

16. The method of claim 1, wherein said gasoline fuel formulations are selected from a group consisting of formulations having a DCN range from 27.2 to 32.4, equivalent to an (R+M)/2 octane range from 62.5 to 80.7, an aromatics content of 12.7% to 35.6%, a paraffin content range from 60.3% to 79.3%, and combinations thereof.

17. The method of claim 1, further including:
said diesel fuel formulations being selected from a group consisting of formulations having a DCN range from 23.4 to 45, equivalent to a cetane number range from 19.4 to 45.9, an aromatic content ranging from 13.9% to 65.4%, and combinations thereof; and
said gasoline fuel formulations being selected from a group consisting of formulations having a DCN range from 27.2 to 32.4, equivalent to an (R+M)/2octane range from 62.5 to 80.7, an aromatics content of 12.7% to 35.6%, a paraffin content range from 60.3 to 79.3, and combinations thereof.

18. The method of claim 1, wherein the HOCI engine includes direct injection.

19. A method for selecting a fuel formulation for a plurality of HCCI engines, comprising the steps of:
identifying each one of a plurality of fuel formulations by a derived cetane number (DCN) determined in accordance with ASTM method D6890, wherein said plurality of fuel formulations include both diesel fuel formulations and gasoline fuel formulations;
testing said plurality of fuel formulations to determine the ignitability of each; and
running each of said plurality of HCCI engines on each one of the tested said plurality of fuel formulations to determine or match for each engine of a given compression ratio (CR) the fuel formulation that maximizes the load capability and load range thereof.

20. The method of claim 19, further including the step of tabulating the results of said running step for future reference in selecting a fuel formulation for a HCCI engine.

21. The method of claim 19, further including the step of tabulating the DCN numbers of said plurality of fuel formulations matched to the CR of said plurality of each of said DI HCCI engines, respectively, for optimizing the operation thereof, thereby facilitating the future selection of a fuel formulation to run a given DI HCCI engine.

22. The method of claim 19, further including controlling particulate emissions from said DI HCCI engine by making the aromatic content of diesel boiling range fuels less than 60 wt. %.

23. The method of claim 19, further including controlling particulate emissions from said DI HCCI engine by making the aromatic content of gasoline boiling range fuels less than 40 wt. %.

24. The method of claim 19, wherein in said identifying step the plurality of fuel formulations have DCN numbers ranging from 0 to 100.

25. The method of claim 19, wherein said diesel fuel formulations have a DCN range from 23.4 to 45.0, respectively.

26. The method of claim 25, wherein said diesel fuel formulations have an aromatic content ranging from 13.9% to 65.4%.

27. The method of claim 19, wherein said gasoline fuel formulations have a DCN range from 27.2 to 32.4.

28. The method of claim 27, wherein said gasoline fuel formulations have an aromatic content ranging from 12.7% to 35.6%.

29. The method of claim 19, wherein the HCCI engine includes direct injection.

30. The method of claim 20, further including the step of:
identifying each one of said plurality of fuel formulations by an (R+M)/2 octane number.

31. The method of claim 20, further including the step of:
identifying each one of said plurality of fuel formulations by a cetane number.

32. The method of claim 21, further including the step of establishing a relationship between the derived cetane numbers and (R+M)/2 octane.

33. The method of claim 21, further including the step of:
establishing a relationship between derived cetane numbers and cetane.

34. The method of claim 19, wherein said diesel fuel formulations are selected from a group consisting of formulations having a DCN range from 23.4 to 45, equivalent to a cetane number range from 19.4 to 45.9, an aromatic content ranging from 13.9% to 65.4%, and combinations thereof.

35. The method of claim 19, wherein said gasoline fuel formulations are selected from a group consisting of formulations having a DCN range from 27.2 to 32.4, equivalent to an (R+M)/2 octane range from 62.5 to 80.7, an aromatics content of 12.7% to 35.6%, a paraffin content range from 60.3% to 79.3%, and combinations thereof.

36. The method of claim 19, further including:
said diesel fuel formulations being selected from a group consisting of formulations having a DCN range from 23.4 to 45, equivalent to a cetane number range from 19.4 to 45.9, an aromatic content ranging from 13.9% to 65.4%, and combinations thereof; and
said gasoline fuel formulations being selected from a group consisting of formulations having a DCN range from 27.2 to 32.4, equivalent to an (R+M)/2 octane range from 62.5 to 80.7, an aromatics content of 12.7% to 35.6%, a paraffin content range from 60.3% to 79.3%, and combinations thereof.

* * * * *